United States Patent
Gruter et al.

(10) Patent No.: US 8,314,260 B2
(45) Date of Patent: Nov. 20, 2012

(54) HYDROXYMETHYLFURFURAL ETHERS AND ESTERS PREPARED IN IONIC LIQUIDS

(75) Inventors: Gerardus Johannes Maria Gruter, Heemstede (NL); Leo Ernest Manzer, Wilmington, DE (US); Ana Sofia Vagueiro De Sousa Dias, Haarlem (NL); Frits Dautzenberg, San Diego, CA (US); Jindra Purmova, Arnhem (NL)

(73) Assignee: Furanix Technologies B.V., Amsterdam (NL)

( * ) Notice: Subject to any disclaimer, the term of this patent is extended or adjusted under 35 U.S.C. 154(b) by 493 days.

(21) Appl. No.: 12/517,112

(22) PCT Filed: Sep. 5, 2008

(86) PCT No.: PCT/EP2008/007429
§ 371 (c)(1),
(2), (4) Date: Sep. 16, 2009

(87) PCT Pub. No.: WO2009/030512
PCT Pub. Date: Mar. 12, 2009

(65) Prior Publication Data
US 2010/0081833 A1    Apr. 1, 2010

(30) Foreign Application Priority Data
Sep. 7, 2007 (EP) .................................... 07017571

(51) Int. Cl.
*C07D 307/02* (2006.01)
(52) U.S. Cl. ........ 549/500; 549/479; 549/483; 549/484; 549/485
(58) Field of Classification Search .................. 549/479, 549/483, 484, 485, 488, 500, 501
See application file for complete search history.

(56) References Cited

U.S. PATENT DOCUMENTS 7,317,116 B2 * 1/2008 Sanborn ........................ 549/483

FOREIGN PATENT DOCUMENTS

| EP | 0 641 854 A1 | | 3/1995 |
| GB | 925812 | * | 5/1963 |
| WO | 2006/063220 A2 | | 6/2006 |
| WO | 2007/104514 A2 | | 9/2007 |
| WO | 2007/104515 A1 | | 9/2007 |

OTHER PUBLICATIONS

March et al, March's Advanced Organic Chemistry, reactions, mechanisms, and structure, 5th ed., 2001, pp. 338-341.*
Carlini et al, "Selective synthesis of 2-ethyl-1-hexanol from n-butanol through the Guerbet reaction by using bifunctional catalysts based on copper or palladium precursors and sodium butoxide", Journal of Molecular Catalysis A: Chemical 212 (2004) pp. 65-70.
Marker, T.L., "Scientific and Technical Information (STI) for Financial Assistance Recipients and Non-M&O/M&I Contractors", United States Department of Energy (DOE), Announcement, DOE F 241.3, 2005.
Roman-Leshkov, Y., et al., "Phase Modifiers Promote Efficient Production of Hydroxymethylfurfural from Fructose", Science, vol. 312, p. 1933-1937, 2006.
Moreau, C., et al., "Dehydration of Fructose and Sucrose in 5-Hydroxymethylfurfural in the Presence of 1-H-3-Methyl Imidazolium Chloride Acting both as Solvent and Catalyst", Journal of Molecular Catalysis A: Chemical 253, p. 165-169, 2006.
Zhao, H., et al., "Metal Chlorides in Ionic Liquid Solvents Convert Sugars to 5-Hydroxymethylfurfural", Science, vol. 316, p. 1597-1600, 2007.

* cited by examiner

*Primary Examiner* — Taylor Victor Oh
(74) *Attorney, Agent, or Firm* — Hoffmann & Baron, LLP

(57) ABSTRACT

Accordingly, the current invention provides a method for the manufacture of an ether or ester of 5-hydroxymethyl-furfural by reacting a hexose-containing starting material or HMF with an alcohol or an organic acid dissolved into an ionic liquid, using a metal chloride as catalyst.

14 Claims, No Drawings

HYDROXYMETHYLFURFURAL ETHERS AND ESTERS PREPARED IN IONIC LIQUIDS

CROSS-REFERENCE TO RELATED APPLICATIONS

This application is the National Stage of International Application No. PCT/EP2008/007429, filed Sep. 5, 2008, which claims the benefit of European Application No. EP 07017571.6, filed Sep. 7, 2007, the contents of which is incorporated by reference herein.

TECHNICAL FIELD

The present invention concerns a method for the manufacture of an ether or an ester of 5-hydroxymethylfurfural (5-(hydroxymethyl)-2-furaldehyde, or HMF) from biomass. More in particular, the present invention concerns a method wherein ionic liquids are used in the manufacture of the ether or ester (jointly referred to as RMF).

BACKGROUND ART

Fuel, fuel additives and various chemicals used in the petrochemical industry are derived from oil, gas and coal, all finite sources. Biomass, on the other hand, is considered a renewable source. Biomass is biological material (including biodegradable wastes) which can be used for the production of fuels or for industrial production of e.g. fibres, chemicals or heat. It excludes organic material which has been transformed by geological processes into substances such as coal or petroleum.

Production of biomass derived products for non-food applications is a growing industry. Bio-based fuels are an example of an application with strong growing interest.

Biomass contains sugars (hexoses and pentoses) that may be converted into value added products. Current biofuel activities from sugars are mainly directed towards the fermentation of sucrose or glucose into ethanol or via complete breakdown via Syngas to synthetic liquid fuels. EP 0641 854 describes the use of fuel compositions comprising of hydrocarbons and/or vegetable oil derivatives containing at least one glycerol ether to reduce particulate matter emissions.

More recently, the acid catalysed reaction of fructose has been re-visited, creating HMF as an intermediate of great interest. Most processes investigated have the disadvantage that HMF is not very stable at the reaction conditions required for its formation. Fast removal from the water-phase containing the sugar starting material and the acid catalyst has been viewed as a solution for this problem. Researchers at the University of Wisconsin-Madison have developed a process to make HMF from fructose. HMF can be converted into monomers for plastics, petroleum or fuel extenders, or even into fuel itself. The process by prof. James Dumesic and co-workers first dehydrates the fructose in an aqueous phase with the use of an acid catalyst (hydrochloric acid or an acidic ion-exchange resin). Salt is added to salt-out the HMF into the extracting phase. The extracting phase uses an inert organic solvent that favors extraction of HMF from the aqueous phase. The two-phase process operates at high fructose concentrations (10 to 50 wt %), achieves high yields (80% HMF selectivity at 90% fructose conversion), and delivers HMF in a separation-friendly solvent (DUMESIC, James A, et al. "Phase modifiers promote efficient production of Hydroxymethylfurfural from fructose". Science. 30 Jun. 2006, vol. 312, no. 5782, p. 1933-1937). Although the HMF yields from this process are interesting, the multi-solvent process has cost-disadvantages due to the relatively complex plant design and because of the less than ideal yields when cheaper and less reactive hexoses than fructose, such as glucose or sucrose, are used as a starting material. HMF is a solid at room temperature which has to be converted in subsequent steps to useful products. Dumesic has reported an integrated hydrogenolysis process step to convert HMF into dimethylfuran (DMF), which is assumed to be an interesting gasoline additive.

In WO 2006/063220 a method is provided for converting fructose into 5-ethoxymethylfurfural (EMF) at 60° C., using an acid catalyst either in batch during 24 hours or continuously via column elution during 17 hours. Applications of EMF were not discussed.

Also in copending patent application PCT/EP2007/002145 the manufacture of HMF ethers are described, including the use of such ethers as fuel or fuel additive. Indeed, both the methyl ether and the ethyl ether (methoxymethylfurfural, or MMF; ethoxyethylfurfural or EMF) were prepared and tested. PCT/EP2007/002146 is a similar copending patent application, but now in respect of the manufacture of HMF esters.

Claude Moreau et al. found that the acid-catalyzed dehydration of fructose may be performed in a microbatch reactor at using 1-H-3-methyl imidazolium chloride ("Dehydration of fructose and sucrose into 5-hydroxymethylfurfural in the presence of 1-H-3-methyl imidazolium chloride acting both as solvent and catalyst", by Claude Moreau et al, Journal of Molecular Catalysis A: Chemical 253 (2006) 165-169). The ionic liquid is a very suitable solvent, there is no decomposition of the produced 5-hydroxymethylfurfural and the fructose is nearly quantitatively transformed into HMF. When sucrose is used (a disaccharide of glucose and fructose) the sugar is nearly quantitatively transformed into HMF and unreacted glucose. It would thus appear that the method of Moreau et al is of no use in the preparation of fuel components based on glucose.

Zhao et al found that the catalytic conversion of sugars into HMF may be improved, using an ionic liquid and certain metal halides dissolved in 1-alkyl-3-methylimidazolium chloride as catalyst. Small amounts of levulinic aced are formed in these reactions ("Metal Chlorides in Ionic Liquid Solvents Converts Sugars to 5-Hydroxymethylfurfural", by Haibo Zhao et al, *Science*. 316, 1597 (15 Jun. 2007).

The current inventors set out to prepare a fuel or fuel component that is not contaminated by levulinic acid and that may be made from various biomass derived sugars, including glucose. Surprisingly, it has been found that such can be achieved by performing the reaction in the presence of an organic acid or alcohol as co-reactant, converting the sugar into an ether or ester of HMF.

DISCLOSURE OF INVENTION

Accordingly, the current invention provides a method for the manufacture of an ether or ester of 5-hydroxymethylfurfural by reacting a hexose-containing starting material or HMF with an alcohol or an organic acid, dissolved into an ionic liquid, using a metal chloride as catalyst.

When the reaction product of the above method is used as such or when it is used as an intermediate for a subsequent conversion, the selectivity of the reaction is preferably high as the product is preferably pure. However, when the reaction product of the above method is used as a fuel, a fuel additive or as a fuel or a fuel additive intermediate, the reaction product does not necessarily need to be pure. Indeed, in the preparation of fuel and fuel additives from biomass, which in itself is a mixture of various monosaccharides, disaccharides and polysaccharides, the reaction product may contain non-interfering components such as levulinic acid derivatives and/or derivatives of pentoses and the like. For ease of reference, however, the method and the reaction product are described in terms of the reaction of a hexose-containing starting material, resulting in an ether or ester of HMF. Also within the scope of the invention is the reaction of HMF with the alcohol or acid, since HMF is believed to be produced as intermediate from the hexose-containing starting material.

The current invention also provides for the use of the reaction product made according to the present invention as fuel or as fuel additive. Fuels for blending with the product of the present invention include but are not limited to gasoline and gasoline-ethanol blends, kerosene, diesel, biodiesel (refers to a non-petroleum-based diesel fuel consisting of short chain alkyl (methyl or ethyl) esters, made by transesterification of vegetable oil, which can be used (alone, or blended with conventional petrodiesel), Fischer-Tropsch liquids (for example obtained from GTL, CTL or BTL gas-to-liquids/coal-to-liquids/biomass to liquids processes), diesel-biodiesel blends and green diesel and blends of diesel and/or biodiesel with green diesel (green diesel is a hydrocarbon obtained by hydrotreating biomass derived oils, fats, greases or pyrolysis oil; see for example the UOP report OPPORTUNITIES FOR BIORENEWABLES IN OIL REFINERIES FINAL TECHNICAL REPORT, SUBMITTED TO: U.S. DEPARTMENT OF ENERGY (DOE Award Number: DE-FG36-05GO15085). The product is a premium diesel fuel containing no sulfur and having a cetane number of 90 to 100). Fuels for blending with the product of the present invention may also include one or more other furanics, wherein the expression furanics is used to include all derivatives of furan and tetrahydrofuran. The invention also provides a fuel composition comprising a fuel element as described above and the reaction product made according to the present invention.

MODE(S) FOR CARRYING OUT THE INVENTION

Biomass resources are well known. The components of interest in biomass are the mono-, di- or polysaccharides (hereinafter referred to as hexose-containing starting material). Suitable 6-carbon monosaccharides include but are not limited to fructose, glucose, galactose, mannose and their oxidized, reduced, etherified, esterified and amidated derivatives, e.g. aldonic acid or alditol, with glucose being the most abundant, the most economic and therefore the most preferred monosaccharide, albeit less reactive than fructose. On the other hand, the current inventors have also succeeded to convert sucrose, which is also available in great abundance. Other disaccharides that may be used include maltose, cellobiose and lactose. The polysaccharides that may be used include cellulose, inulin (a polyfructan), starch (a polyglucan) and hemi-cellulose. The polysaccharides and disaccharides are converted into their monosaccharide component(s) and dehydrated during the manufacture of the 5-HMF ether.

The alcohol used in the method of the current invention should bear at least one hydroxyl group, which may be in a primary, secondary or even tertiary position. Diols and polyhydric compounds may be used as well. The alcohol may comprise from 3 to 20 carbon atoms, preferably from 3 to 8 carbon atoms. Examples include methanol, ethanol, 1-propanol, 2-propanol, 2-butanol, 2-methyl-1-propanol (isobutanol), 2-methyl-2-propanol (tent-butanol), 2-pentanol (s-amyl alcohol); 2-methyl-1-butanol (p-amyl alcohol); 2-methyl-2-butanol (t-amyl alcohol); 3-methyl-1-butanol (isoamyl alcohol); 2,2-dimethyl-1-propanol (neopentyl alcohol); 2-hexanol; 2-ethyl-1-hexanol (isooctyl alcohol). Also higher alcohols my be used, which includes natural alcohols such as caproic alcohol and caproyl alcohol the like, and which includes synthetic alcohols made by Fisher-Tropsch or by the Guerbet reaction (e.g., 2-ethylhexanol, prepared from butanol; "Selective synthesis of 2-ethyl-1-hexanol from n-butanol through the Guerbet reaction by using bifunctional catalysts based on copper or palladium precursors and sodium butoxide", by Carlo Carlini, Journal of Molecular Catalysis A: Chemical 212 (2004) 65-70). Preferred alcohols used in the method of the current invention include isobutanol, tert-butanol, isoamyl alcohol, isooctyl alcohol. Also blends of alcohols may be used, e.g., of isobutanol and tert-butanol. Also blends of alcohols may be used, e.g., the aforementioned Guerbet alcohols made from a mixed alcohol feed or natural alcohols found as a blend in nature. The current method thus provides an excellent high value outlet for "contaminated" alcohols.

The amount of alcohol used during the manufacture of the HMF ether is preferably at least equimolar on the monosaccharide, but typically is used in much greater excess. Indeed, the alcohol may be used as co-solvent. In such a case, a sufficient amount of alcohol is present to form the HMF ether.

Instead of an alcohol, also an organic acid may be used. Suitably, the organic acid is a mono-carboxylic acid. Preferably the acid is selected from the group consisting of (un)branched aliphatic acids and (un)branched unsaturated acids, more preferably (un)branched aliphatic acids. Still more preferably the organic acid is a C1-C5 (un)branched aliphatic acids, most preferable formic acid, acetic acid, propionic acid, and/or (iso)-butyric acid. In addition to the acid, also the anhydride thereof may be used. Mixtures of acids and/or anhydrides may also be employed.

In view of the good results, the use of an organic acid, and hence the preparation of an ester of 5-hydroxymethylfurfural, is preferred.

The catalyst in the method of the present invention can be selected from amongst any of the metal halides mentioned in by Zhao et al. Examples include $CrCl_2$, $CrCl_3$, $FeCl_2$, $FeCl_3$, $CuCl$, $CuCl_2$, $VCl_3$, $MoCl_3$, $PdCl_2$, $PtCl_2$, $PtCl_4$, $RuCl_3$, or $RhCl_3$. $CrCl_2$ is particularly useful.

The amount of catalyst may vary, depending on the selection of catalyst or catalyst mixture. For instance, the catalyst can be added to the reaction mixture in an amount varying from 0.01 to 40 mole % drawn on the hexose content of the biomass resource, preferably from 0.1 to 30 mole %, more preferably from 1 to 20 mole %.

The temperature at which the reaction is performed may vary, but in general it is preferred that the reaction is carried out at a temperature from 50 to 300 degrees Celsius, preferably from 125 to 250 degrees Celsius, more preferably from 150 to 225 degrees Celsius. In general, temperatures higher than 300 are less preferred as the selectivity of the reaction reduces and as many by-products occur, inter alia caramelisation of the sugar. Performing the reaction below the lowest temperature is also less preferable because of the low reaction rate. If the reactions are carried out above the boiling temperature of water, then the reactions are preferably carried out under pressure, e.g., 10 bar nitrogen or higher.

The hexose-containing starting material is typically dissolved or suspended in a solvent which can be the mixed alcohol reactant, in order to facilitate the reaction. The solvent is a so-called ionic liquid. The latter refers to a class of inert ionic compounds with a low melting point, which may therefore be used as solvent. Examples thereof include 1-alkyl-3-methylimidazolium, 1-alkylpyridinium, N-methyl-N-alkylpyrrolidinium and ammonium ions, whereas a wide range of anions may be employed, from simple halides, which generally inflect high melting points, to inorganic anions such as tetrafluoroborate and hexafluorophosphate and to large organic anions like bis-trifluorsulfonimide, triflate or tosylate. There is no specific limitation to the ionic liquid used in the current invention, albeit that 1-H-3-methyl imidazolium chloride has shown to be a suitable solvent for the biomass-derived sugars. This is therefore a preferred solvent. Use of 1-H-3-methyl imidazolium chloride, is discussed in "Dehydration of fructose and sucrose into 5-hydroxymethylfurfural in the presence of 1-H-3-methyl imidazolium chloride acting both as solvent and catalyst", by Claude Moreau et al, Journal of Molecular Catalysis A: Chemical 253 (2006) 165-169. Also preferred solvents are 1-Ethyl-3-methylimidazolium chloride (EMIM) and H-3-methylimidazolium bis(trifluoromethanesulfonyl)imide (HMIM), and/or mixtures of these solvents.

A sufficient amount of solvent is preferably present to dissolve or suspend the starting material and to limit undesired side-reactions.

The method of the current invention may be carried out in a batch process or in a continuous process, with or without recycle of (part of) the product stream to control the reaction temperature (recycle via a heat exchanger). For instance, the method of the invention can be performed in a continuous flow process. In such method, homogenous catalysts may be used and the residence time of the reactants in the flow process is between 0.1 second and 10 hours, preferably from 1 second to 1 hours, more preferably from 5 seconds to 20 minutes.

Alternatively, the continuous flow process may be a fixed bed continuous flow process or a reactive (catalytic) distillation process with a heterogeneous acid catalyst (meaning a solid catalyst). To initiate or regenerate the heterogeneous acid catalyst or to improve performance, an inorganic or organic acid may be added to the feed of the fixed bed or reactive distillation continuous flow process. In a fixed bed process, the liquid hourly space velocity (LHSV) can be from 1 to 1000, preferably from 5 to 500, more preferably from 10 to 250 and most preferably from 25 to 100 $min^{-1}$.

The above process results in a stable HMF ether or ester, which can then be used as such or be converted into a further derivative before being used as fuel and/or as fuel additive.

Examples are enclosed to illustrate the method of the current invention and the suitability of the products prepared therefrom as fuel. The examples are not meant to limit the scope of the invention.

EXAMPLE 1

In a batch experiment, 50 mg of substrate (glucose or fructose) and 250 mg of 1-Ethyl-3-methylimidazolium chloride (EMIM) or 500 mg of a mixture of EMIM and H-3-methylimidazolium bis(trifluoromethanesulfonyl)imide (HMIM) were loaded in a Teflon lined reactor with 7.5 ml volume. 1 ml of acetic acid was added and the mixture reacted under nitrogen (12.5 bar) in the presence of $CrCl_2$ as catalyst for 3 h at 100° C. Two products were observed in the UV spectra and identified as HMF and 5-acetoxy methyl furfural (AMF). Selectivities and conversions for catalysts used in this example can be found in table below.

The substrate conversions and the selectivities and yields were calculated according to the formulas:

Conversion=100*$[n_0(\text{substrate})-n_t(\text{substrate})]/n_0$ substrate

Selectivity=100*$n_t(\text{product})/[n_0(\text{substrate})-n_t(\text{substrate})]$ Yield=100*$n_t(\text{product})/n_0$ substrate, Where:
$n_0$—the initial number of moles
$n_t$—the number the moles of a compound at time "t".

| Substrate | Solvent | Amount of catalyst [mg] | Y HMF (%) | Y AMF (%) |
|---|---|---|---|---|
| Glucose | EMIM | 2.0 | 1.3 | 5.1 |
| Glucose | EMIM + HMIM | 2.0 | 1.8 | 6.9 |
| Glucose | EMIM + HMIM | 3.5 | 1.9 | 9.2 |
| Fructose | EMIM | 2.0 | 22.3 | 71.5 |
| Fructose | EMIM + HMIM | 2.0 | 29.2 | 59.4 |
| Fructose | EMIM + HMIM | 3.5 | 19.6 | 74.8 |

EXAMPLE 2

In a batch experiment, 50 mg of substrate (glucose or fructose) and 250 mg of 1-Ethyl-3-methylimidazolium chloride (EMIM) or 500 mg of a mixture of EMIM and H-3-methylimidazolium bis(trifluoromethanesulfonyl)imide (HMIM) were loaded in a Teflon lined reactor with 7.5 ml volume. 1 ml of propionic acid was added and the mixture reacted under nitrogen (12.5 bar) in the presence of $CrCl_2$ as catalyst for 3 h at 100° C. Two products were observed in the UV spectra and identified as HMF and 5-(propionyloxy)methyl furfural (PMF).

| Substrate | Solvent | Amount of catalyst [mg] | Y HMF (%) | Y PMF (%) |
|---|---|---|---|---|
| Glucose | EMIM | 2.0 | 2.0 | 3.2 |
| Glucose | EMIM + HMIM | 2.0 | 2.2 | 3.2 |
| Glucose | EMIM + HMIM | 3.5 | 1.9 | 3.4 |
| Fructose | EMIM | 2.0 | 33.2 | 52.0 |
| Fructose | EMIM + HMIM | 2.0 | 39.6 | 24.3 |
| Fructose | EMIM + HMIM | 3.5 | 33.0 | 48.7 |

References
DUMESIC, James A, et al. "Phase modifiers promote efficient production of Hydroxymethylfurfural from fructose". Science. 30 Jun. 2006, vol. 312, no. 5782, p. 1933-1937.
WO 2006/063220
PCT/EP2007/002145
PCT/EP2007/002146
MOREAU, Claude, et al. "Dehydration of fructose and sucrose into 5-hydroxymethylfurfural in the presence of 1-H-3-methyl imidazolium chloride acting both as solvent and catalyst", Journal of Molecular Catalysis A: Chemical 253 (2006) p. 165-169.
ZHAO, Haibo et al. "Metal Chlorides in Ionic Liquid Solvents Converts Sugars to 5-Hydroxymethylfurfural", *Science*. 316, 1597 (15 Jun. 2007).

The invention claimed is:
1. A method for the manufacture of an ether or ester of 5-hydroxymethylfurfural by reacting a hexose-containing starting material or HMF with an alcohol or an organic acid dissolved into an ionic liquid as solvent comprising compounds having alkyl-3-methylimidazolium, 1-alkylpyridinium, N-methyl-N-alkylpyrrolidinium or ammonium ions as cation and halides, inorganic anions and organic anions as anion, using further a metal chloride as an acid catalyst.

2. The method according to claim 1, wherein the acid catalyst is selected from the group consisting of homogeneous and heterogeneous catalysts selected from CrC12, CrC13, FeC12, FeC13, CuC1, CuC12, VC13, MoC13, PdC12, PtC12, PtC14, RuC13, and RhC13.

3. The method according to claim 2, wherein the acid is CrC12.

4. The method according to claim 1, wherein the reaction is performed at a temperature from 50 to 300 degrees Celsius.

5. The method according to claim 1, wherein the hexose-containing starting material is used and wherein the hexose starting material is selected from the group consisting of starch, amylose, galactose, cellulose, hemi-cellulose, glucose-containing disaccharides, glucose and fructose.

6. The method according to claim 1, wherein an ester of 5-hydroxymethylfurfural is prepared by reacting a hexose-containing starting material or HMF with an organic acid.

7. The method according to claim 6, wherein a mono-carboxylic acid or anhydride or a mixture of acids and/or anhydrides is used, selected from the group consisting of (un)branched aliphatic acids and (un)branched unsaturated acids, and the anhydrides thereof.

8. The method according to claim 7, wherein a C1-C5 (un)branched aliphatic acid or anhydride or a mixture of C1-C5 (un)branched aliphatic acids and/or anhydrides is used.

9. The method according to claim 1, wherein the inorganic anion is tetrafluoroborate or hexafluorophosphate.

10. The method according to claim 1, wherein the organic anion is bis-trifluorosulfonimide, triflate or tosylate.

11. The method according to claim 1, wherein the ionic liquid is selected from the group consisting of 1-H-3-methyl imidazolium chloride, 1-ethyl-3-methylimidazolium chloride (EMIM), H-3-methylimidazolium bis(trifluoromethanesulfonyl) imide (HMIM) and mixtures thereof.

12. The method according to claim 4, wherein the reaction is performed at a temperature from 125 to 250 degrees Celsius.

13. A method for the manufacture of an ether or ester of 5-hydroxymethylfurfural by reacting a hexose-containing starting material or HMF with an alcohol or an organic acid dissolved into an ionic liquid as solvent, using a further metal chloride as catalyst, wherein the ionic liquid used as solvent is selected from the group consisting of compounds having bis-trifluorosulfonimide, triflate and tosylate as anion.

14. The method according to claim 13, wherein the ionic liquid used as solvent is selected from the group consisting of compounds having 1-alkyl-3-methylimidazolium, 1-alkylpyridinium, N-methyl-N-alkylpyrrolidinium and ammonium ions as cation.

* * * * *